US00PP35425P2

(12) United States Plant Patent
Horvath

(10) Patent No.: US PP35,425 P2
(45) Date of Patent: Oct. 17, 2023

(54) ***LEUCANTHEMUM SUPERBUM* PLANT NAMED 'FLOWER POWER'**

(50) Latin Name: *Leucanthemum superbum*
Varietal Denomination: Flower Power

(71) Applicant: Brent Arpad Horvath, Fontana, WI (US)

(72) Inventor: Brent Arpad Horvath, Fontana, WI (US)

( * ) Notice: Subject to any disclaimer, the term of this patent is extended or adjusted under 35 U.S.C. 154(b) by 45 days.

(21) Appl. No.: 17/803,809

(22) Filed: Dec. 5, 2022

(51) Int. Cl.
*A01H 5/02* (2018.01)
*A01H 6/14* (2018.01)

(52) U.S. Cl.
USPC ..... Plt./285

(58) Field of Classification Search
USPC ..... Plt./263.1, 284, 285
See application file for complete search history.

*Primary Examiner* — Karen M Redden

(57) ABSTRACT

A new and distinct variety of *Leucanthemum superbum* plant as shown and described, characterized by white ray florets and yellow disc florets on upright branched stems and a medium to large height.

1 Drawing Sheet

Figure 1:
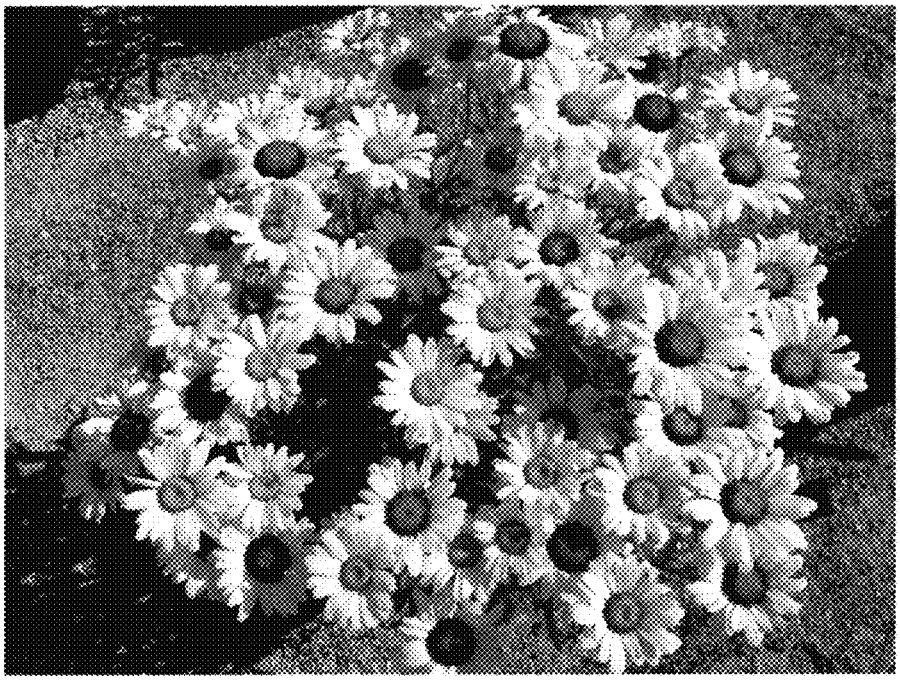

Latin name: *Leucanthemum superbum.*
Cultivar name: 'Flower Power'.

BACKGROUND OF THE INVENTION

The present invention relates to a new and distinct plant of *Leucanthemum superbum* plant named 'Flower Power' characterized by white ray florets and yellow disc florets on upright branched stems and a medium to large height.

The new *Leucanthemum superbum* was raised as an open pollinated seedling from a controlled breeding program, the seed was sown as *Leucanthemum superbum* 'Hebron Hardy' not patented, at a nursery in Hebron, Ill. in 2015. The selection of the new plant was due to its white ray florets and yellow disc florets on upright branched stems and a medium to large height.

Asexual division, and cutting propagation have been the means of reproduction. Propagation has taken place at a nursery in Hebron, Ill. since 2016. The new *Leucanthemum* has shown to be stable and identical in reproduction after rooting over 2000 plants from 2016 to 2022. No plants of the new *Leucanthemum superbum* have been sold in this country, or anywhere in the world, prior to the filing of this application, nor has any disclosure of the new plant been made prior to the filing of this application with the exception of that which was disclosed by the inventor and his company, Intrinsic Perennial Gardens, Inc within one year of filing of this application and was derived directly from the inventor, including the company Garden Choice offering of the plant.

SUMMARY OF THE INVENTION

The new *Leucanthemum superbum* plant named 'Flower Power' characterized by white ray florets and yellow disc florets upright branched stems and a medium to large height have been observed to be unique and stable.

Plants of the new *Leucanthemum* can be compared to plants of *Leucanthemum superbum* 'Becky' not patented. 1. The new *Leucanthemum superbum* plant has a mature size measuring 60-75 cm high and 65-85 cm wide while *Leucanthemum superbum* 'Becky' measures 100-120 cm high and over 100 cm wide. 2. The new *Leucanthemum superbum* plant has an upright branched habit while *Leucanthemum superbum* 'Becky' has an open habit. 3. The new *Leucanthemum superbum* plant has smaller foliage approximately 30 mm wide while *Leucanthemum superbum* 'Becky' has foliage that reaches approximately 35 mm wide.

Plants of the new *Leucanthemum superbum* can also be compared to the seed parent plant *Leucanthemum superbum* 'Hebron Hardy' not patented. 1. The new plant has a uniform height since it is produced asexually from vegetative division and cutting propagation while the seed parent is produced from seed and the height and plant size varies.

Plants of the new *Leucanthemum superbum* can also be compared to plants of *Leucanthemum superbum* 'Banana Cream', U.S. Plant Pat. No. 23,181. 1. The new plant inflorescence color is white ray florets and yellow disc florets while the inflorescence color of the *Leucanthemum superbum* 'Banana Cream' plant is yellow ray florets and yellow disc florets.

DESCRIPTION OF PHOTOGRAPHS

FIG. 1. A close up of a blooming 2 year old plant in July from the top.

Figure 2:
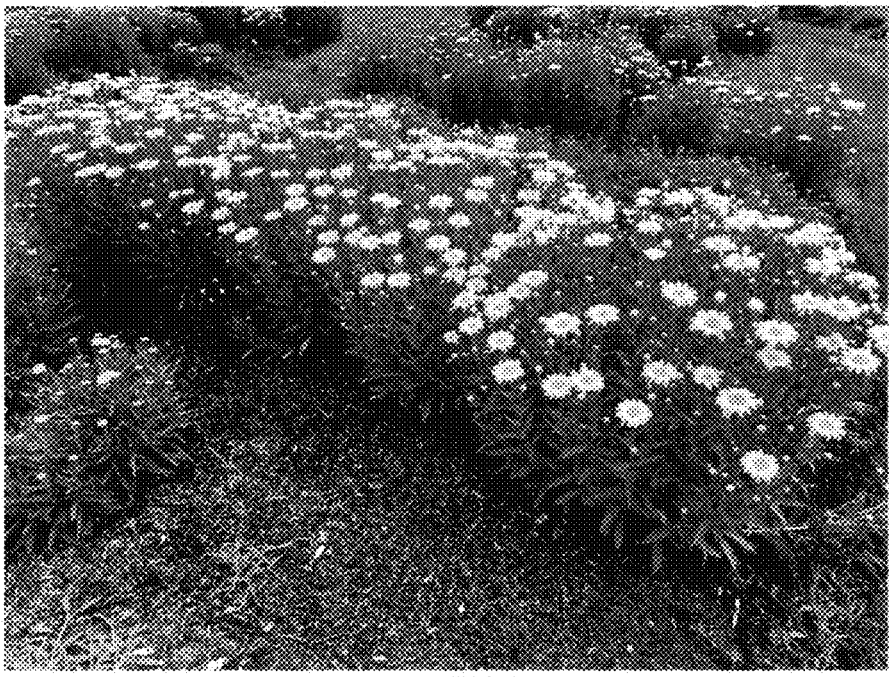

FIG. 2. A row of 2 year old plants in the ground budding and starting to bloom in June.

DETAILED BOTANICAL DESCRIPTION

In the following description, color references are made to The Royal Horticultural Society Colour Chart from 2001. Plants used for the description were grown for two seasons at a nursery in Hebron, Ill. US. Measurements and numerical values represent averages of typical plants.

Botanical classification: *Leucanthemum superbum* cultivar Flower Power.

Parentage: Male or pollen parent an unknown and unnamed *Leucanthemum superbum*, female or seed parent *Leucanthemum superbum* 'Hebron Hardy'.

Propagation: Vegetative division and cutting propagation.

Plant description: Overall habit of the new *Leucanthemum* is an upright branched clump, with stems topped by inflorescences of white ray florets and yellow disc florets that open in mid to late June.

*Plant height.*—60-75 cm.

*Plant width.*—65-85 cm.

*Primary stem diameter.*—4 mm.

*Primary and secondary stem description.*—Branching, with 20 or more leaves.

Roots: Fibrous thin and branched, color close to 155 D.

Propagation: Tip cuttings take 2-3 weeks to produce roots. Leaves get smaller as they go up the stem:

*Primary and lateral stem texture.*—Sparsely pubescent with hairs up to 1 mm long.

*Secondary stem description.*—Average 2 lateral stems per primary stem.

*Secondary stem length.*—18 cm.

*Secondary stem diameter.*—2-3 mm.

*Secondary stem internodes.*—3-4 cm.

Foliage:

*Type.*—Deciduous.

*Leaf arrangement.*—Alternate.

*Length.*—8-12 cm.

*Width.*—30 mm.

*Shape.*—Spatulate.

*Apex.*—Acute.

*Base.*—Cuneate.

*Margin.*—Dentate.

*Texture.*—Smooth, glabrous, moderately glossy.

*Adaxial leaf description.*—Color is 137 A.

*Abaxial leaf description.*—Color is 146 A.

*Adaxial leaf vein color.*—137 A.

*Abaxial leaf vein color.*—146 A.

Peduncle: Strong, stiff puberulent up to 18 cm long, 3-4 mm wide.

Bud:

*Bud shape.*—Flattened globular.

*Bud length.*—8 mm.

*Bud diameter.*—13 mm.

*Bud color.*—Both 138 B and 138 C.

Inflorescence:

*Inflorescence type.*—Composite on basal flowering stems.

*Position.*—Terminal.

*Number of inflorescences per plant.*—Approximately 85.

*Arrangement.*—Disc and ray florets.

*Disc floret.*—Four fused petals, yellow color 15 A.

*Disc floret diameter.*—2 mm at apex, 1-2 mm at base.

*Disc floret shape.*—Rotate.

*Disc floret length.*—7 mm.

*Disc floret width.*—1 mm.

*Disc floret apex.*—Acute.

*Disc floret margin.*—Entire.

*Disc floret count.*—Approximately 200 per inflorescence.

*Ray floret size.*—32 mm length and 10 mm width.

*Ray floret color.*—Both Adaxial and Abaxial surfaces are close to 155 C.

*Ray floret aspect.*—Upright.

*Ray floret shape.*—Oblanceolate.

*Ray floret apex.*—Tridentate.

*Ray floret base.*—Cuneate.

*Ray floret margin.*—Entire.

*Ray floret count.*—Approximately 36 per inflorescence.

*Ray floret texture.*—Both the upper and lower surfaces are smooth, glabrous.

*Androecium.*—Five stamens connate around the style. Anther — Five, connate in to a tube. 3 mm long and 1 mm wide. On disc florets only. Color 17 A. Filaments — Fused at apex, 3 mm long and less than 1 mm wide. Color close to 155 C. Pollen — on Disc florets only, color 17 A.

*Gynoecium.*—On ray florets and disc florets, 9 mm long, excerted. Style — 5 mm long and less than 1 mm wide, color 145 C. Stigma — Bifid, 1 mm long and less than 1 mm wide. Color 7 B.

*Involucre.*—Made up of three to four layers of phyllaries, 1 cm long and 3 cm wide.

*Phyllaries.*—Lanceolate, glabrous, apex acute, base truncate, 35 per head in three to four rows, 1 cm long, 3 mm wide. Color — Adaxial and abaxial 137 C at the center, margins N199 B.

*Fruit.*—Achene, pointed at the base, rounded at the top. Color — close to 199 A with some striations near 156 D.

*Overall inflorescence size.*—8-10 cm or more across in diameter with ray florets.

*Bloom period and duration.*—Mid to late June through July.

*Blooming habit.*—Domed, terminal on up to 60-75 cm stems.

*Scent.*—No scent noticed.

*Disease resistance.*—Resistance to diseases common to *Leucanthemum* has not been observed on plants grown under nursery conditions.

*Hardiness.*—Plants of the new *Leucanthemum superbum* have been observed to be hardy to USDA Zone 5.

I claim:

1. A new and distinct variety of *Leucanthemum superbum* plant named 'Flower Power' as shown and described, characterized by white ray florets and yellow disc florets on upright branched stems and a medium to large height.

* * * * *